United States Patent [19]

Lukase et al.

[11] Patent Number: 5,057,016

[45] Date of Patent: Oct. 15, 1991

[54] FORCEPS HAVING REPLACEABLE TIPS FOR REMOVING A DENTAL PROSTHETIC

[75] Inventors: Stephen P. Lukase, Glendale, Ariz.; Thomas A. Lukase, 2670 Greentree La., La Jolla, Calif. 92037

[73] Assignee: Thomas A. Lukase, Glendale, Ariz.

[21] Appl. No.: 601,668

[22] Filed: Oct. 23, 1990

[51] Int. Cl.⁵ ............................................. A61C 3/16
[52] U.S. Cl. ................................... 433/160; 433/159
[58] Field of Search ................................ 433/159, 160

[56] References Cited

U.S. PATENT DOCUMENTS

| 831,307 | 9/1906 | Spahn | 433/160 |
| 3,866,324 | 2/1975 | Walser | 433/160 |
| 4,197,647 | 4/1980 | Goldenthal | 433/159 |

FOREIGN PATENT DOCUMENTS

| 2412113 | 9/1975 | Fed. Rep. of Germany | 433/159 |
| 2254939 | 7/1975 | France | 433/159 |

Primary Examiner—John J. Wilson
Attorney, Agent, or Firm—Cahill, Sutton & Thomas

[57] ABSTRACT

A pair of dental forceps, whether configured for anterior, premolar or molar teeth, includes a pair of tips having removable cushioning and gripping inserts for conformingly gripping and frictionally retaining a respective dental prosthetic device, such as a crown or bridge, to be removed without imposing stress concentrations sufficient to mar or damage the dental prosthetic device.

20 Claims, 3 Drawing Sheets

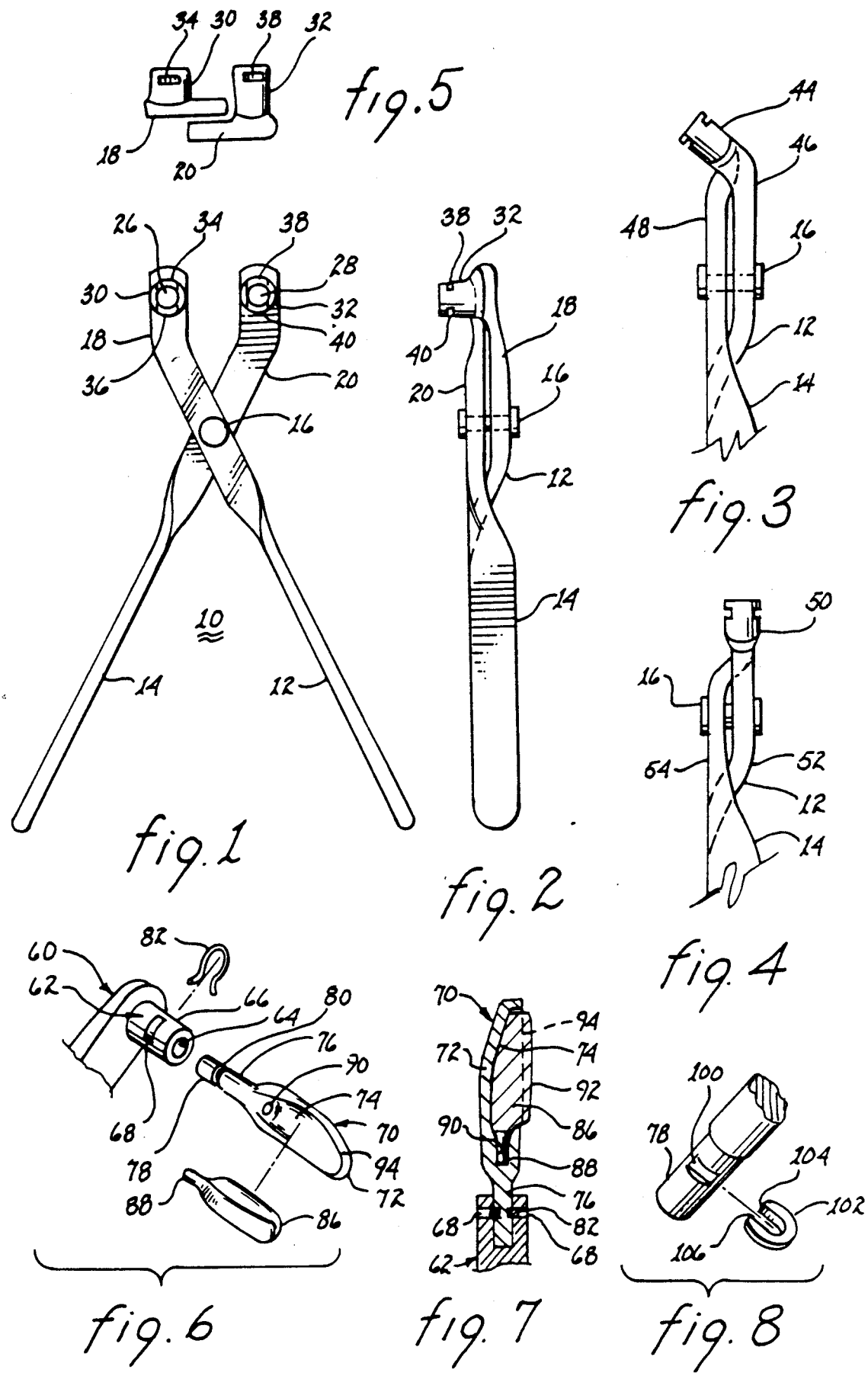

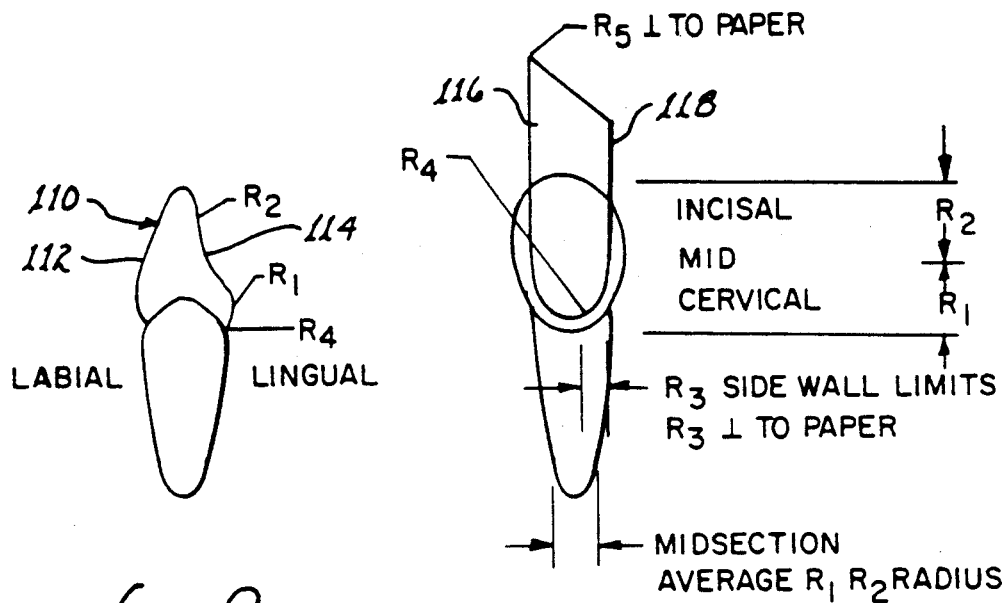
fig. 9a
fig. 9b
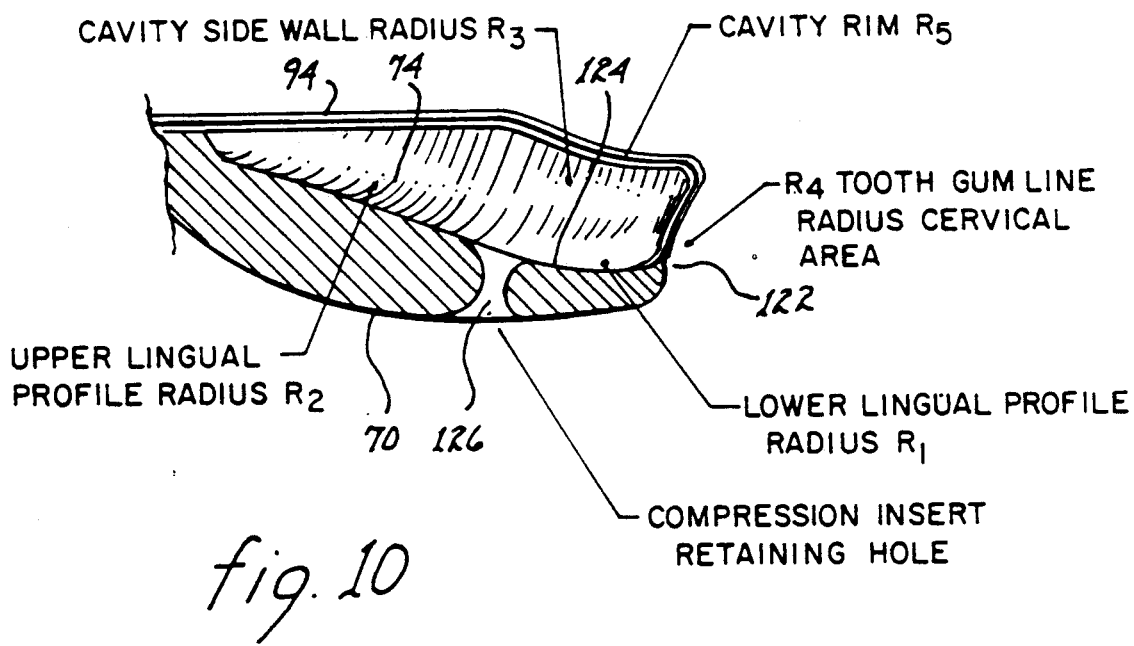
fig. 10

FORCEPS HAVING REPLACEABLE TIPS FOR REMOVING A DENTAL PROSTHETIC

BACKGROUND OF THE INVENTION

1. Field of the Invention

The present invention relates to dental implements and, more particularly, to forceps and gripping elements for removing dental prosthetic devices.

2. Description of the Prior Art

Dental forceps, particularly configured for use upon the anterior, premolar or molar teeth have been available for years for purposes of extracting a tooth. These forceps have jaws particularly angled of and of a length to facilitate grasping a particular tooth. During tooth extraction, it is very important that a firm grip of the tooth be achieved and it is of no consequence if the enamel of the tooth cracks or if the tooth is otherwise damaged.

The forceps used for extracting teeth have been developed over a period of many decades to provide an effective combination of gripping a tooth and ease of manipulation of the gripped tooth to effect the extraction process. Primarily, the developmental work has been directed to the length and angulation of the gripping jaws.

To remove a crown for purposes of reattaching it more securely to develop a better seal or for adjustment purposes, it is very important that the crown not be aesthetically damaged or physically distorted. To use a conventional pair of extraction forceps for this purpose presents a real problem for the following reasons. The jaws of the forceps may damage the surface of the crown even though a good firm grip is established. If the forceps are only lightly squeezed to avoid damage to the crown, the jaws may slip from the crown and cause injury to the patient or damage to other teeth or restorations. For these reasons, many dentists use their fingers, and particularly their fingernails, to grasp the cervical ridge of the crown to dislodge and extract the crown. Since not all dentists have sufficient power in their fingers for this purpose, crown removal is a problem. Similarly, not all dentists have sufficiently robust fingernails to withstand the forces imposed without bending and causing substantial pain to the dentist. A potential problem of fungal infection also exists.

Various devices have been developed over the years to attempt to solve the above enumerated problems. In the 1920s, a clamp forceps was developed which cooperated with a detachably attached rubber dam to minimize damage to a crown while retaining sufficient gripping and extracting force. Regrettably, this device was difficult and awkward to use as a practical matter. Some time later, a pair of forceps was developed which included a pair of opposed curved surfaces lined with resilient material for gripping a crown. These forceps were very difficult to use for all teeth due to the different requirements of grip and manipulation imposed by the placement of each tooth within the mouth.

A yet further device was developed which is of a plier like configuration having one jaw of the pair of jaws oriented to contact and bear against the proximal edge of the crown while the second jaw was penetrably inserted through a passageway cut in the top of the crown to bear against the underlying tooth. In situations where the underlying tooth is little more than a post, this device is ineffective. Moreover, the requirement for a passageway through the cusp of the crown necessitated repair and reconstruction of the crown prior to remounting.

SUMMARY OF THE INVENTION

A pair of extraction forceps includes detachably attachable differently angled jaws selected to correspond with the tooth supporting the crown or bridge to be removed. Removable inserts are disposed in the jaws for gripping with sufficient force to permit removal of the crown or bridge while preventing damage or disfigurement to the surface and structure of the crown or bridge. The replaceabilty of the inserts permits autoclaving or other sterilizing procedures of the forceps and jaws; the inserts are intended to be for one time use and to be disposable. The jaws can be selected for a particular configuration compatible with the type and location of the prosthetic device to be removed and they are detachably attached by a snap fit to permit rapid exchange.

It is therefore a primary object of the present invention to provide apparatus for grasping and removing a dental prosthetic device without damaging it.

Another object of the present invention is to provide an extraction tool for extracting a dental prosthetic device.

Still another object of the present invention is to provide a resilient conformable insert for the jaws of a pair of forceps to grasp and remove a prosthetic device.

Yet another object of the present invention is to provide a selection of jaw elements interchangeably replaceable upon the jaws of a pair of dental forceps for grasping and extracting a dental prosthetic device.

A further object of the present invention is to provide a removable insert for use with removable jaws of dental forceps to extract dental prosthetic devices.

A still further object of the present invention is to provide a method for extracting a dental prosthetic device without damaging the device during extraction.

A yet further object of the present invention is to provide a method for firmly grasping but not damaging a prosthetic device to be removed.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 1 illustrates a pair of forceps having female fittings for receiving a pair of jaws;

FIG. 2 illustrates a side view of the pair of forceps;

FIGS. 3 and 4 illustrate adaptations of the forceps shown in FIGS. 1 and 2;

FIG. 5 illustrates an end view of the fittings attached to the forceps shown in FIGS. 1 and 2;

FIG. 6 illustrates a tip and mating insert usable with each of the fittings shown in FIG. 5;

FIG. 7 illustrates a cross section of the tip and insert;

FIG. 8 illustrates a device for securing the tip to the fitting of the forceps;

FIGS. 9a and 9b illustrate representative side and rear elevational views of premolar and anterior crowns mounted upon a tooth;

FIG. 10 illustrates a cross sectional view of a tip;

DESCRIPTION OF THE PREFERRED EMBODIMENT

Figure 12B:
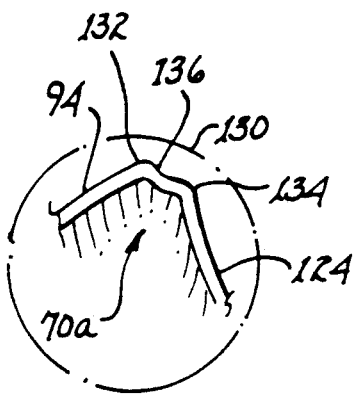
FIGS. 12a and 12b illustrate modifications to the tip for accommodating cervical ridge anomalies.

To assist a dentist in extracting teeth, numerous extraction forceps have been developed for groups of teeth which represent similar or related accessibility, direction of extraction and manipulation impediments. These forceps can generally be categorized as being suitable for anterior, premolar or molar teeth. It is to be understood that further gradations also exist. As shown in FIGS. 1 and 2, a pair of forceps 10 includes handles 12,14 pivotally attached to one another by pivot means 16. Jaws 18,20 associated with handles 12,14, respectively, may extend generally planar with the handles or may be slightly bent, as shown in side view in FIG. 2 or substantially bent as shown in side view in FIG. 3. Female fittings are disposed at the ends of each of jaws 18 and 20, respectively. Each of these fittings includes a cavity (26,28) defined by a cylinder (30,32) extending from the respective jaw 18,20. A pair of opposed slots 34,36 and 38,40 is formed in diametrically opposed sections of cylinders 30,32, respectively. As shown in FIG. 2, the cylinders extend perpendicularly to the major axis of the respective jaws.

FIGS. 3 and 4 illustrate variant orientations of the fittings to assist the dentist in extracting particular anterior, pre molar or molar dental prosthetic devices. For example, fittings 44, shown in FIG. 3, are oriented at an angle of approximately 45° with respect to the major axis of jaws 46,48. Fittings 50, shown in FIG. 4, are oriented in general alignment with the major axis of jaws 52,54. To accommodate overlap of jaws 18,20, as shown in FIG. 5, fittings 30,32 may be of different length to place their respective ends in a common plane. The degree of angular orientation of the fittings primarily dictates the type of tooth with which the pair of forceps is to be used.

For tooth extraction purposes, the jaws of a pair of forceps are of surgical steel or similar material which permits a very firm rigid grip of a tooth to be extracted. Whether the act of gripping and manipulating the tooth during extraction results in damage to the tooth enamel or the structure of the tooth is generally not of significance.

When a crown is to be removed in the event the seal for the crown has been compromised, to repair the crown or to adjust the crown, it is important to prevent damage to the crown during the act of removal. Were such damage to occur, reconstruction or replacement of the crown would result in substantial expense which should be avoided. Because of the fragility of crowns, a dentist often must rely upon the strength of his fingers to effect removal since implements for this purpose and which have a low probability of causing damage to the crown do not exist. All dentists do not have sufficient strength in their fingers to effect removal of a crown. Furthermore, the space or volume available within the oral cavity to manually grip a crown may be a limiting factor of the ease with which a crown can be removed.

Referring to FIG. 6 there is illustrated a representative jaw 60 (like jaws 18,20) having a fitting 62 extending perpendicularly therefrom. The fitting includes a cavity 64 formed in a cylindrical element 66 of the fitting. A pair of diametrically opposed slots, of which slot 68 is shown, are in communication with cavity 64. A tip 70 includes a scoop 72 having a generally elongated recess 74 formed therein. Recess 74 has a geometric cavity contour of the labial/buccal or lingual surface relating to the crown to be removed. A support element 76 extends from one end of the scoop. It includes a cylindrical member 78 configured for penetrable engagement with cavity 64. A groove 80 circumscribes cylindrical member 78. Upon insertion of cylindrical member 78 into cavity 64, groove 80 is coincident with the slots (68) in fitting 62. A clip 82 is configured to penetrate the opposed slots in the fitting and partially engage groove 80. The engagement between clip 82 and groove 80 will create an interfering fit to preclude withdrawal of cylindrical member 78 from within cavity 64. By having the groove cylindrical, tip 70 may rotate about the axis of cylindrical member 78 in response to forces imposed.

An insert 86 is configured to mate with and nest within recess 74. It also includes a tang 88 for penetrable insertion into passageway 90, which passageway may be coincident with the longitudinal axis of the tip. As particularly illustrated in FIG. 7, insert 86 includes a face 92, which face extends above, or is displaced from perimeter 94 of tip 72.

The displacement of face 92 of insert 86 will tend to preclude physical contact between tip 70 and the crown or other dental prosthetic to be removed whereby damage due to pressure exerted by the hard surface of tip 70 would be precluded.

Insert 86 can be relatively easily removed from the supporting tip by simply grasping the extending portion and pulling the insert out of recess 74. Thereafter, the pair of forceps and tips may be autoclaved or otherwise sterilized without concern for damage to the insert. It is contemplated that each pair of inserts would be used only one time and would be disposable.

Preferably, insert 86 is of resilient flexible material, such as a rubber composition or a plastic composition, which is suitable for molding or other fabrication. Sufficient resistance to compressibility must be present to prevent the pressures exerted by pair of tips (70) from coming into contact with the dental prosthetic to be removed. Furthermore, the insert must exert sufficient friction upon the surface of the dental prosthetic, such as a crown to prevent slippage without the application of sufficient compressive forces which might collapse or otherwise damage the crown upon disengagement from the underlying supporting tooth.

Under certain circumstances, it may be preferable to inhibit rotation of tip 70 about its longitudinal axis. By substituting a pair of opposed indentations (of which indentation 100 is shown) for groove 80 and by incorporating an essentially rigid clip 102 for clip 82, rotation of the tip will be inhibited. That is, interior edges 104,106 of clip 102 will nest within opposed indentations 10 and inhibit rotation of cylindrical member 78 due to the resulting interference with the longitudinal edges.

The configuration of each of tips 70 and inserts 86 is preferably commensurate with the surface of the dental prosthetic to be grasped by the respective tip/insert. Such correspondence will tend to distribute uniform forces along the contacted dental prosthetic to minimize the likelihood of damage or deformation. Moreover, a greater effective gripping area of essentially uniformly applied forces will result and extraction of the dental prosthetic will be eased.

A representative tooth mounted premolar and anterior crown 110 is illustrated in FIGS. 9a and 9b. Outward surface 112 is generally referred to as the labial surface while inward surface 114 is referred to as the lingual surface. These are the two surfaces contacted by the jaws of forceps during extraction. Furthermore, it is generally 60% of these surfaces which is gripped. This portion of the lingual surface is identified as the area within the limit of lines 116,118 (the cavity rim associated with the radius R5 in FIG. 10). To promote and ensure a non slipping grip, the forceps jaws preferably conform with the various curvatures depicted by designations R1, R2, R3, R4 and R5 in the cervical, mid and incisal portions of the crown.

FIG. 10 illustrates a cross section of a typical recess or depression 74 (see FIGS. 6 and 7) formed in a tip 70. The depression illustrated is representative of the curvature of the lingual surface 114, it being understood that the curvature of the depression used in conjunction with the labial surface 112 would be commensurately configured. More particularly, the curvature or radius at each of locations R1, R2, R3, R4 and R5 would be specifically contoured to the mating curvature of the crown. That is, R1 would be equivalent with the lower lingual profile, R2 would be equivalent to the upper lingual profile, R3 would be equivalent to the cavity sidewall, R4 would be equivalent to the tooth gum line in the cervical area and R5 would be equivalent to the curvature of the rim of the depression commensurate with the contact area of the lingual surface extending longitudinally along the tooth generally proximate lines 116,118 (see FIG. 9b).

Figure 11A:
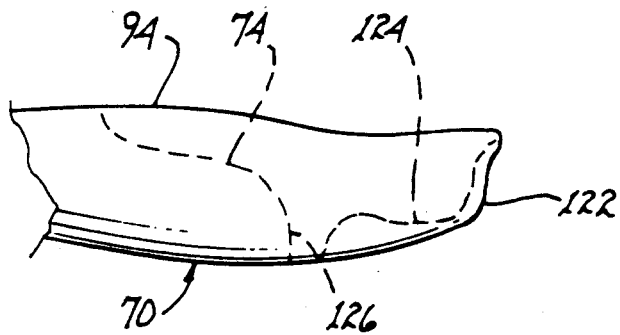
FIGS. 11a, 11b and 11c illustrate cross sectional and top views of the tip segment shown in FIG. 10.
Figure 11C:
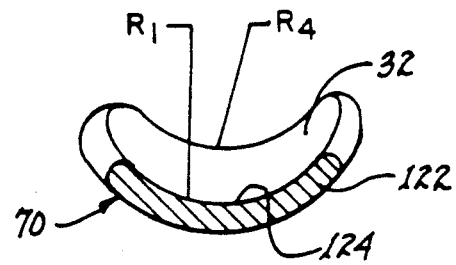
Figure 11B:
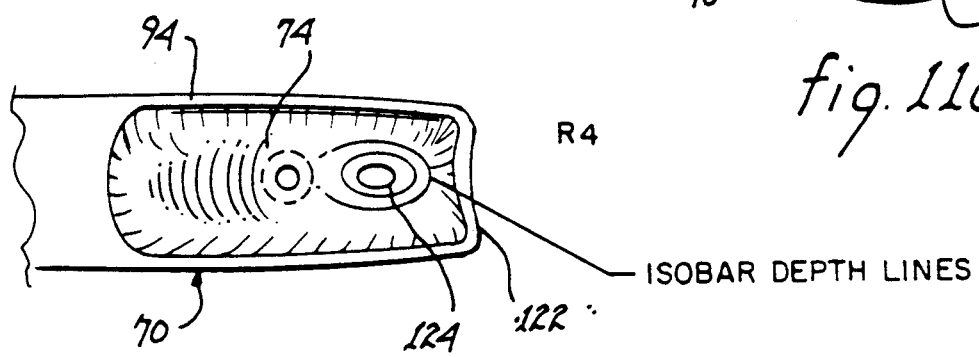

Referring jointly to FIGS. 11a, 11b and 11c, further views of depression 74 in tip 70 are illustrated. Terminal end 122 includes a curved edge 124 conforming in general to the curvature attendant R1 of crown 110. The remaining curvatures and contours of depression 74 generally conform with that of the mid third section of the lingual surface of tooth 110.

The insert to be fitted within the tip and its depression depicted in FIG. 10 and in FIGS. 11a, 11b and 11c will compressingly conform with the depression to receive the commensurate lingual or labial surface of a crown and exert uniform forces thereagainst upon gripping of the crown by the forceps. Such uniformity of gripping forces will reduce stress concentrations to minimize damage or deformation to the crown and minimize the likelihood of slipping while providing a high degree of control to manipulation of the crown during extraction.

The tip depicted in FIGS. 10, 11a, 11b and 11c may include a passageway 126 for penetrably receiving a tang extending from the approximate center bottom of the insert. This tang assists in installing the insert by pushing the tang into the passageway and pulling on the protruding tang until the insert becomes seated. Simultaneous pushing on the insert will assist the seating of the insert. Preferably, the insert extends above and across edge 94 of tip 70 to preclude contact between the crown to be gripped and the tip.

Figure 12A:
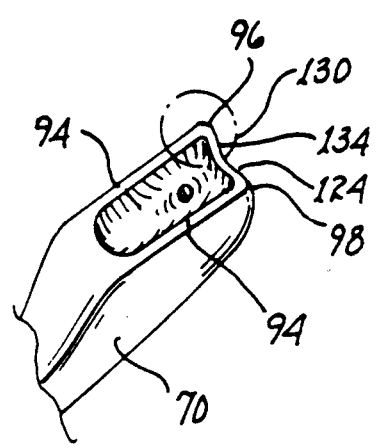

FIGS. 12a and 12b partially illustrate a variant 70a of tip 70 for accommodating anomalies of the dental prosthetic to be removed. In tip 70, edges 94 join with terminal edge 124 at locations which define relatively sharp points. Depending upon the structure and configuration of both the tooth and associated dental prosthetic, there may be anomalies in the area of the cervical ridge and primarily in the mesio/distal length. The presence of sharp points 96,98 on tip 70 may create difficulties in effecting facile gripping and removal of the dental prosthetic. To eliminate such cause for difficulty, variant tip 70a may be used. In the area of one of the pair of sharp points identified within circle 130 in FIG. 12a, segments of edges 94,124 extending from the junction to locations identified by 132,134 are removed. The resulting edge, identified by numeral 136 in FIG. 12b, eliminates point 96 present in tip 70. A similar modification is performed on edges 94,124 forming point 98 to replace this point with an edge equivalent to edge 136. Such modification to tip 70 will not negatively affect the efficacy of edge 124 in engaging the cervical ridge of the dental prosthetic as a functional equivalent of a dentist's fingernail and it will accommodate the aforementioned possible anomalies.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A pair of forceps for gripping in a non damaging manner a dental prosthetic device to effect removal of the dental prosthetic device, said pair of forceps comprising in combination:
   a) a pair of handles for manipulating said pair of forceps;
   b) a pair of jaws extending from said pair of handles, each jaw being an extension of one handle of said pair of handles;
   c) means for pivotally interconnecting said pair of handles to relocate said pair of jaws toward and away from one another;
   d) a pair of studs, one of said pair of studs extending from each jaw of said pair of jaws;
   e) a pair of tips for contacting opposed sides of the dental prosthetic device;
   f) means for detachably attaching one tip of said pair of tips to each stud of said pair of studs;
   g) a recess disposed in each tip of said pair of tips; and
   h) an insert of a pair of inserts being disposed in each of said recesses for contacting the dental prosthetic device, each insert of said pair of inserts including means for restraining contact between the respective one of said tips and the dental prosthetic device.

2. The apparatus as set forth in claim 1 wherein each stud of said pair of studs includes a longitudinal axis and wherein said attaching means includes means for attaching each of said pair of tips in alignment with the longitudinal axis of the respective one of said pair of studs.

3. The apparatus as set forth in claim 1 wherein each stud of said pair of studs includes a longitudinal axis extending perpendicularly from the respective jaw of said pair of jaws.

4. The apparatus as set forth in claim 1 wherein each stud of said pair of studs includes a longitudinal axis extending in general alignment with the respective jaw of said pair of jaws.

5. The apparatus as set forth in claim 1 including means for detachably attaching each insert of said pair of inserts with the respective one of said pair of tips.

6. The apparatus as set forth in claim 5 wherein said insert attaching means includes a passageway extending from said recess and a tang extending from said insert for insertion into said passageway.

7. The apparatus as set forth in claim 1 wherein said restraining means includes a segment of said insert extending out from within the respective one of said recesses.

8. The apparatus as set forth in claim 7 wherein said insert is of resilient flexible material.

9. The apparatus as set forth in claim 1 wherein said tip attaching means includes a cavity disposed in said stud and a member extending from said tip for insertion within said cavity of the respective one of said studs.

10. A pair of forceps for gripping in a non damaging manner a dental prosthetic device to effect removal of the dental prosthetic device, said pair of forceps comprising:

a) a pair of pivotally attached handles, said pair of handles including a pair of jaws;

b) a pair of tips for contacting opposed sides of the dental prosthetic device, each tip of said pair of tips including a longitudinal axis;

c) means for detachably attaching one tip of said pair of tips to each jaw of said pair of jaws, said detachably attaching means including means for accommodating movement of each tip of said pair of tips only along and about the longitudinal axis of the respective tips; and d) an insert attached to each tip of said pair of tips for contacting the dental prosthetic device and for restraining direct contact between said pair of tips and the dental prosthetic device.

11. The apparatus as set forth in claim 10 wherein each tip of said pair of tips includes a recess for receiving one of said inserts.

12. The apparatus as set forth in claim 11 including means for securing each insert of said pair of inserts with the respective one of said recesses.

13. The apparatus as set forth in claim 12 wherein said securing means includes a passageway extending from each recess of said pair of tips and a tang extending from each of said pair of inserts for retention within the respective one of said passageways.

14. The apparatus as set forth in claim 11 wherein each of said recesses is disposed in a side of the respective one of said pair of tips.

15. The apparatus as set forth in claim 14 wherein each of said inserts extends out of the respective one of said recesses.

16. The apparatus as set forth in claim 11 wherein one of said recesses is configured to mate with on side of the dental prosthetic and wherein the other of said recesses is configured to mate with the other side of the dental prosthetic.

17. The apparatus as set forth in claim 10 wherein said detachably attaching means includes means for locking in place each tip of said pair of tips while accommodating rotation of each tip of said pair of tips about its respective longitudinal axis.

18. The apparatus as set forth in claim 10 wherein said locking means comprises means for defining a cylindrical cavity in each jaw of said pair of jaws to receive one end of one tip of said pair of tips.

19. The apparatus as set forth in claim 18 including means for removably retaining said one end of each tip of said pair of tips in the respective one of the cavities.

20. The apparatus as set forth in claim 19 wherein each one of said removably retaining means comprises a clip.

* * * * *